United States Patent [19]

Plueddemann

[11] 4,344,860

[45] Aug. 17, 1982

[54] STABILIZATION OF SILICATES USING SALTS OF SUBSTITUTED NITROGEN OR SULFUR CONTAINING SILICONATES

[75] Inventor: Edwin P. Plueddemann, Midland, Mich.

[73] Assignee: Dow Corning Corporation, Midland, Mich.

[21] Appl. No.: 248,131

[22] Filed: Mar. 30, 1981

[51] Int. Cl.³ .......................... C07F 7/02; C07F 7/08; C07F 7/10; C09K 3/00

[52] U.S. Cl. .............................. 252/389 R; 556/401; 252/78.3; 568/701; 422/14; 422/16; 422/17

[58] Field of Search ................ 556/401; 568/701; 252/389 R, 78.3

[56] References Cited

U.S. PATENT DOCUMENTS

| | | | |
|---|---|---|---|
| 2,389,802 | 11/1945 | McGregor et al. | 556/401 |
| 3,884,950 | 5/1975 | Koda et al. | 556/401 |
| 4,070,343 | 1/1978 | Kishimoto et al. | 556/401 X |
| 4,230,632 | 10/1980 | Chapman | 556/401 |

*Primary Examiner*—Paul F. Shaver
*Attorney, Agent, or Firm*—Robert L. McKellar

[57] ABSTRACT

Salts of substituted nitrogen or sulfur containing siliconates are effective stabilizers for aqueous silicates in such applications as treating boiler water, geothermal water and other aqueous silicates. They are also useful in antifreeze and coolant solutions.

112 Claims, No Drawings

STABILIZATION OF SILICATES USING SALTS OF SUBSTITUTED NITROGEN OR SULFUR CONTAINING SILICONATES

BACKGROUND OF THE INVENTION

This invention deals with novel salts of substituted nitrogen or sulfur containing siliconates which are effective stabilizers for aqueous silicates, silica sols and other silica containing water, such as boiler water, geothermal water, antifreeze and coolant solutions.

Aqueous silicates are known as metal corrosion inhibitors for aqueous systems. One of the major disadvantages of such silicates, however, has been the fact that they are unstable and after prolonged use at elevated temperatures they tend to gel and eventually precipitate out of solution. There have been many efforts, therefore, to stabilize silicates so that they could be more persistant in their corrosion inhibiting properties.

Arthur N. Pines et al. in U.S. Pat. Nos. 3,312,622 and 3,198,820 describe combinations of siliconate-silicate polymers as corrosion inhibitors. Although the patent does not specifically describe the stabilization of silicates, it is very obvious from the specification that the so-called "novel organosilicon polymer" does in fact contribute to the persistency of the corrosion inhibition of the siliconate-silicate polymers of that invention. The novelty, as pointed out therein, is the use of silyl carboxylate salts in conjunction with the silicates. Such materials are discussed as enhancing the corrosion inhibition of common antifreeze compositions and as overcoming disadvantages of other prior art corrosion inhibitors such as handling and dispensing of the antifreezes; selective corrosion inhibition of certain metals, poor shelf life, tendency to attack rubber hoses, excessive foaming in use and the causing of alcohols to decompose.

In later issued patents, U.S. Pat. Nos. 3,341,469 and 3,337,496, Pine et al. describe another system that was found useful for inhibiting corrosion in aqueous alcohol compositions. It consisted of a mixture of an alkyl silsesquioxane, a siloxane modified with a cyanoalkyl or carbinol group and, a silicate. There materials are stated as being "remarkably soluble in aqueous liquids". Further, the compositions are alleged to overcome many of the above mentioned disadvantages.

Another U.S. Pat. No. 3,948,964, issued Apr. 6, 1976, describes the stabilization of partially hydrolyzed silicic acid esters using stabilizers selected from the organic compounds such as cyclic ethers, ether alcohols, carboxylic acid esters and ketones. Such stabilized materials are described as binders for zinc dust pigments and the like.

In U.S. Pat. No. 3,960,576, issued June 1, 1976, there is disclosed the use of organic phosphonates in conjunction with alkaline oxide silicates as corrosion inhibitors for metal surfaces. It is stated therein that in addition to its corrosion inhibiting properties, the materials have the advantage of preventing the crystallization and deposition of dissolved solids which tend to precipitate on hot heat transfer surfaces.

Finally, there is a disclosure in a co-pending U.S. pat. application Ser. No. 891,584, filed Mar. 30, 1978, now abandoned in the name of Edwin P. Plueddemann, showing the use of siliconates of silylalkyl phosphonates to stabilize aqueous silicates.

Thus, what has now been discovered is the use of certain sulfur or nitrogen containing siliconate salts to stabilize soluble silicates in order to overcome the problems associated with the prior art products.

THE INVENTION

The invention disclosed herein consists of a method of stabilizing soluble silicates comprising adding to the soluble silicates a siliconate selected from a group consisting essentially of (I) a siliconate having the general formula

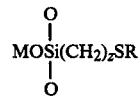

and (II) a siliconate having the general formula

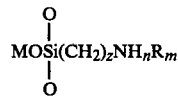

wherein, in both formulas, M is selected from a group consisting essentially of (i) alkali metal cations and (ii) tetraorganoammonium cations and z has a value of 2 or 3, wherein in formula (I), R is selected from a group consisting essentially of —CH$_2$COOM, —CH$_2$CH$_2$COOM,

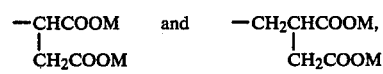

and wherein in formula (II), n has a value of 0 or 1; m has a value of 1 or 2, the sum of n+m is 2 and R is selected from a group consisting essentially of —CH$_2$COOM, —CH$_2$CH$_2$COOM,

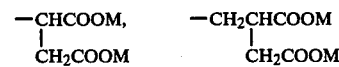

and —(CH$_2$)$_z$N(CH$_2$COOM)$_2$ when n is 0 and m is 2, and R is selected from a group consisting essentially of

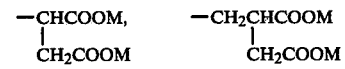

and —(CH$_2$)$_z$NH$_p$R'$_q$ when n is 1 and m is 1, p has a value of 0 or 1, q has a value of 1 or 2 and the sum of p+q is 2 wherein R' is selected from a group consisting of

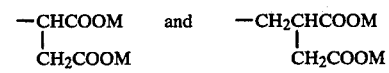

when p is 1 and q is 1 and R' is selected from a group consisting of —CH$_2$COOM, —CH$_2$CH$_2$COOM,

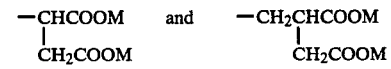

when p is 0 and q is 2, wherein M and z have the same meaning as set forth above.

This invention also consists of an improved corrosion inhibiting alcohol composition comprising a combination of (A) an alcohol; (B) a corrosion inhibiting amount of a composition which is selected from (I) a siliconate having the general formula

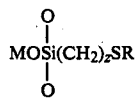

and (II) a siliconate having the general formula

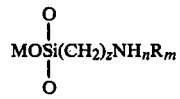

wherein, in both formulas, M is selected from a group consisting essentially of (i) alkali metal cations and (ii) tetraorganoammonium cations and z has a value of 2 or 3, wherein in formula (I), R is selected from a group consisting essentially of —CH$_2$COOM, —CH$_2$CH$_2$COOM,

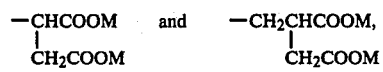

and wherein in formula (II), n has a value of 0 or 1; m has a value of 1 or 2, the sum of n+m is 2 and R is selected from a group consisting essentially of —CH$_2$COOM, —CH$_2$CH$_2$COOM,

and —(CH$_2$)$_z$N(CH$_2$COOM)$_2$ when n is 0 and m is 2, and R is selected from a group consisting essentially of

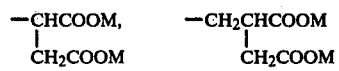

and —(CH$_2$)$_z$NH$_p$R'$_q$ when n is 1 and m is 1, p has a value of 0 or 1, q has a value of 1 or 2 and the sum of p+q is 2, and (C) a soluble silicate represented by the general formula

wherein M has the meaning above and a has a value of 1–3.

This invention further deals with a composition of matter which comprises (A) 0.1 to 20 mole percent of a siliconate selected from a group consisting essentially of (I) a siliconate having the general formula

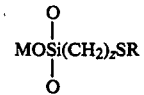

and (II) a siliconate having the general formula

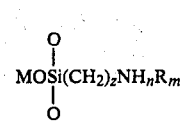

wherein, in both formulas, M is selected from a group consisting essentially of (i) alkali metal cations and (ii) tetraorganoammonium cations and z has a value of 2 or 3, wherein in formula (I), R is selected from a group consisting essentially of —CH$_2$COOM, —CH$_2$CH$_2$COOM,

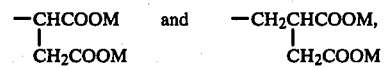

and wherein the formula (II), n has a value of 0 or 1; m has a value of 1 or 2, the sum of n+m is 2 and R is selected from a group consisting essentially of —CH$_2$COOM, —CH$_2$CH$_2$COOM,

and —(CH$_2$)$_z$N(CH$_2$COOM)$_2$ when n is 0 and m is 2, and R is selected from a group consisting essentially of

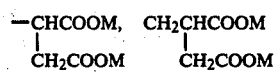

and —(CH$_{2l}$)$_z$NH$_p$R'$_q$ when n is 1 and m is 1, p has a value of 0 or 1, q has a value of 1 or 2 and the sum of p+q is 2, and (B) 80 to 99.9 mole percent of a soluble silicate represented by the general formula

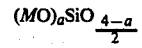

wherein M has the meaning above and a has a value of 1–3.

This invention also deals with a method of inhibiting metal corrosion in an aqueous medium by adding to the aqueous medium a composition consisting of a siliconate selected from a group consisting of (I) a siliconate having the general formula

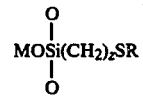

and (II) a siliconate having the general formula

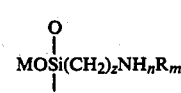

wherein, in both formulas, M is selected from a group consisting essentially of (i) alkali metal cations and (ii) tetraorganoammonium cations and z has a value of 2 or 3, wherein in formula (I), R is selected from a group consisting essentially of —CH$_2$COOM, —CH$_2$CH$_2$COOM,

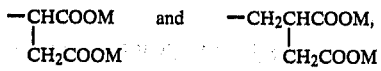

and wherein in formula (II), n has a value of 0 or 1; m has a value of 1 or 2, the sum of n+m is 2 and R is selected from a group consisting essentially of —CH$_2$COOM, —CH$_2$CH$_2$COOM,

and —(CH$_2$)$_z$N(CH$_2$COOM)$_2$ when n is 0 and m is 2, and R is selected from a group consisting essentially of

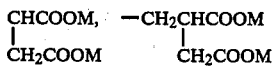

and —(CH$_2$)$_z$NH$_p$R$'_q$ when n is 1 and m is 1, p has a value of 0 or 1, g has a value of 1 or 2 and the sum of p+q is 2 wherein R' is selected from a group consisting of

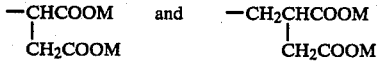

when p is 1 and q is 1 and R' is selected from a group consisting of —CH$_2$COOM, —CH$_2$CH$_2$COOM,

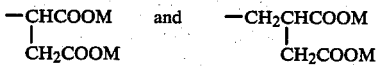

when p is 0 and q is 2, wherein M and z have the same meaning as set forth above.

Further, this invention deals with a method of inhibiting metal corrosion in an aqueous medium wherein the siliconate salts described above are used in conjunction with soluble silicates, that is, where the siliconate salts and the soluble silicate are combined and used to treat aqueous systems to prevent metal corrosion.

Finally, this invention deals with aqueous alcohol compositions which are antifreezes, coolants and concentrates for use in engines having water cooling systems.

As can be observed from the above disclosure, the key to the inventive concepts herein is the use of certain, specifically defined, siliconate salts shown by the above formulas. It should be noted that there are two formulas used to describe the siliconate salts that are useful in this invention. The formula for the siliconate salts differs depending on whether the siliconate salt contains a sulfur atom or a nitrogen atom.

In the above formulas, M can be selected from two different cationic groups which are the alkali metal cations and the tetraorganoammonium cations. Thus, M for purposes of this invention can be selected from sodium, potassium, lithium and rubidium while the tetraorganoammonium cations can be selected from tetra(alkyl)ammonium cations; tetra- (mixed aryl-alkyl and mixed aralkyl-alkyl ammonium cations and the tetra(hydroxyalkyl) ammonium cations. Preferred are tetra(methyl)ammonium, tetra(ethyl)ammonium, phenyltrimethyl ammonium, benzyltrimethyl ammonium and tetra(hydroxyethyl) ammonium cations. Also considered within the scope of this invention are the polyvalent cations produced by converting polyamines such as quanidine or ethylenediamine to poly ammonium hydroxides (See U.S. Pat. No. 3,341,469, supra).

The unoccupied valences (not shown in the formulae for the sake of simplicity) of the oxygen atoms attached to the silicon atoms of the siliconate salts can be occupied by M or hydrogen or another silicon atom as long as there is at least one oxygen atom on the silicon atom occupied by an alkali metal cation or a tetraorganoammonium cation.

The siliconate salts of this invention can be prepared prior to their use in the inventive compositions herein or the siliconate salts can be prepared in situ.

In both formulas, the group —(CH$_2$)$_z$— represents an alkylene bridge. For purposes of this invention, the value of z is either 2 or 3. It will be noted that this value is critical for purposes of this invention since siliconate salts wherein z has a greater or lesser value than 2 or 3 do not work exceptionally well in this invention.

A further critical aspect of this invention is the type of functional groups which are substituted on the sulfur and nitrogen atoms of the inventive siliconate salts.

Turning first to the sulfur containing siliconate salts represented by the general formula

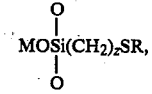

it should be noted that only the groups —CH$_2$COOM, —CH$_2$CH$_2$COOM,

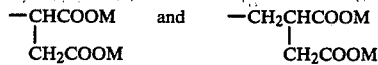

are effective herein.

Thus, representative examples of the sulfur containing siliconate salts useful herein are

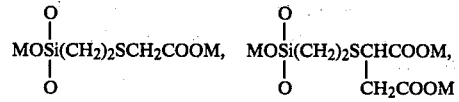

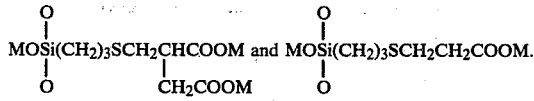

Especially preferred are the sodium and potassium salts of the specific siliconates set forth just above.

Now turning to the nitrogen containing siliconate salts represented by the general formula

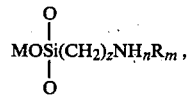

it should be noted that the effective groups herein are determined by the values of n and m in the formula. n has a value of 0 or 1 and m has a value of 1 or 2. In all cases, the sum of n+m has to be 2. R represents the functional groups of the molecule and R changes when n and m are changed. For purposes of this invention, when n is 0 and m is 2, the R group is selected from the groups —CH₂COOM, —CH₂CH₂COOM,

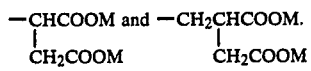

Thus, contemplated within the scope of this invention are the siliconate salts

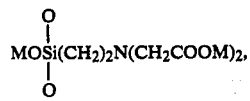

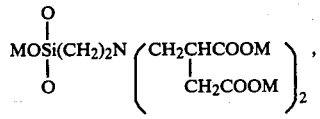

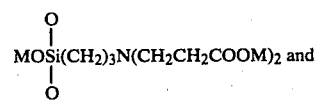

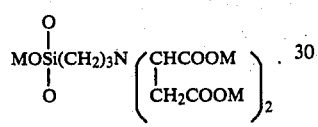

Preferred for this invention are the sodium and potassium salts of the siliconates set forth just above. When n is 1 and m is 1, the R group is selected from the groups

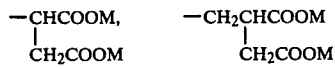

and ⁺(CH₂)$_z$NH$_p$R'$_q$ wherein z has a value of 2 or 3, and wherein q has a value of 1 or 2 and p has a value of 0 or 1 and the sum of q+p is 2. R' is selected from a group consisting of

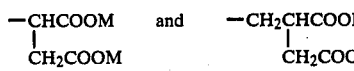

when p is 1 and q is 1 and R' is selected from a group consisting of —CH₂COOM, —CH₂CH₂COOM,

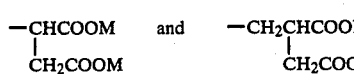

when p is 0 and q is 2. Thus, examples of siliconate salts useful in this invention include

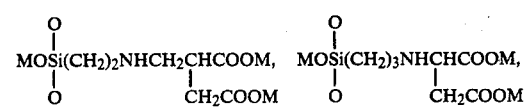

-continued

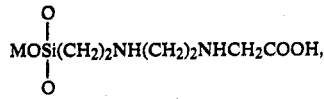

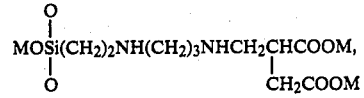

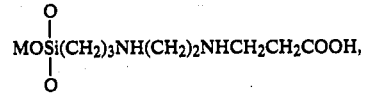

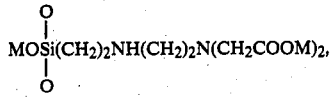

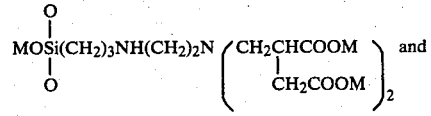

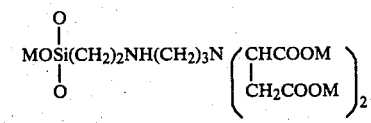

Most preferred are the sodium and potassium salts of the siliconates set forth just above.

As indicated above, the salts of this invention can be prepared prior to use in the inventive compositions of this invention or the salts can be made in situ in the inventive compositions. The salts are prepared from the precursor carboxyorganosiliconates which in turn are prepared by a variety of reactions. Thus, for example, the carboxyfunctional thioethers can be prepared by the methods set forth in U.S. Pat. No. 3,627,806, issued Dec. 14, 1971.

The nitrogen containing siliconate salt precursors are well known and can be prepared by a variety of methods. For example, the reaction of (CH₃O)₃Si(CH₂)₃NH(CH₂)₂NH₂ and 2 moles of acrylic acid yield the precursor dicarboxylic acid. This material can, in turn, be converted to the soluble salt form.

The acids are converted to the soluble salt form by neutralizing with, for example, aqueous NaOH to form the sodium salt.

In practice, the carboxylic acids or their esters are prepared and then hydrolyzed and saponified in the same reaction by using aqueous alkali solutions or the carboxylic acids or their esters are treated with tetraorganoammonium compounds. The resulting products are then used alone or they can be used in conjunction with a silicate as will be explained infra.

The soluble silicates useful in this invention are such materials as alkali metal orthosilicates, alkali metal metasilicates, alkali metal tetrasilicates, the alkali metal disilicates and the tetraorganoammonium silicates.

As mentioned above, this invention deals with a method of stabilizing silicates which are soluble in aqueous systems (whenever solubility of the silicates is referred to in this application, it is intended that the inventor is referring to those known silicates which are soluble in water).

The inventive method herein for stabilizing soluble silicates requires that certain defined siliconate salts be used in aqueous or aqueous-alcoholic systems that already contain soluble silicates but it is also contemplated within the scope of this invention to form a composition from a siliconate salt of this invention and a soluble silicate and use this combination to treat aqueous or aqueous alcoholic systems.

Thus, what is contemplated in this invention is the use of the above defined siliconate salts or combination of such siliconate salts and soluble silicates to treat aqueous or aqueous alcoholic systems to enhance, in the former case, the stabilization of soluble silicates and in the latter case to prevent corrosion of metals.

Such uses therefore include antifreezes, coolants and concentrates for use in automotive engine cooling systems, controlling scale in geothermal power plants, controlling scale in conventional heat exchange systems and the like. Also contemplated within the scope of this invention is the use of the siliconates in household cleaning compositions.

The amount of siliconate salt required to carry out the inventive method herein is dependent on the system in which the siliconate salt is used. Ordinarily, the siliconate salts are useful at a few parts per million concentration to a few weight percent concentration.

When the system requires the addition of the siliconate salts to the soluble silicates before use, the two components are mixed in a ratio of about 0.1 to 20 mole percent of the siliconate salt based on the silicate. Quantities less than 0.1 mole percent have been found to give less than optimum results while quantities greater than about 20 mole percent have been found to be wasteful. For automotive antifreeze applications, it is best to use about 1 part of the siliconate-silicate mixture, based on 100 parts of the aqueous alcohol system, to prevent corrosion.

The amount of siliconate salt that is used when it is not required to premix the siliconate salt with the silicate is about 50 ppm to 5 weight percent based on the weight of the total system it is being used in. For example, if the siliconate salt is used to stabilize soluble silicates in geothermal steam, one only needs to ascertain the amount of soluble silicate that is present in such steam and add an amount of siliconate salt equivalent to 0.1 to 20 mole percent of the siliconate salt based on the silicate present in the steam water. In other water systems, larger quantities may be required. The preferred range of use of the siliconates for all systems within the scope of this invention is about 100 parts per million parts of the total system to 5 parts of the siliconate per 100 parts of the total system.

When the siliconate salt is used with the soluble silicate, there must be water present in the system. Relatively large amounts of water can be used in alcoholic systems or, small amounts, i.e. 80–98 weight percent, of alcohol can be used in the alcohol systems. Thus, the aqueous alcoholic compositions may be "concentrates", coolants, or antifreeze compositions.

The alcohols that are useful in this invention include both monomeric alcohols such as methanol, ethanol, propanol and butanol and polyhydric alcohols such as ethylene glycol, diethylene glycol, triethylene glycol, propylene glycol, glycerol, mixtures of the above and mixtures of the above alcohols with their ethers.

The siliconate salt-soluble silicate combination can be easily prepared by simply mixing the siliconate salt with the soluble silicate. It should be noted that the siliconate salt, when used to stabilize systems already containing the soluble silicate, is simply added to such systems and stirred to homogenize.

The siliconate salt-soluble silicate combination can also be formed in-situ, that is the carboxylic acid or the ester precursor of the siliconate salt can be added to an aqueous or aqueous alcoholic system and the system can be treated with, for example NaOH to saponify and yield the siliconate salt. Sometimes, there may be enough cationic material already in such a system to accomplish the saponification.

It is within the scope of this invention to add various additives which impart special properties such as anti-foam agents, both organic and siloxane based dyes, pH indicators, other inhibitors such as corrosion inhibitors, thickeners and the like.

Now, so that those skilled in the art understand and appreciate the invention, the following examples are offered. These examples should not be construed as limiting that which is set out and claimed as the invention in the appended claims.

EXAMPLE 1

A mixture of 26 gms of methyl acrylate (0.3 mols) and 36.4 gms of $(CH_3O)_3SiCH_2CH_2SH$ was catalyzed by adding 1 ml. of N/2 alcoholic KOH into a 250 ml., round bottomed glass flask, with stirring. An exothermic reaction raised the temperature to 60° C. The mixture was refluxed for 30 minutes and then distilled under vacuum to recover 46 gms of water-white product with a boiling point at 0.7 mm Hg pressure of 115°–125° C. for an 87 percent yield of $(CH_3O)_3Si(CH_2)_2S(CH_2)_2COOCH_3$. $d_4^{20} = 1.115$, $N_D^{25} = 1.4546$. One tenth gram mol (26.8 gms) of this product was saponified by refluxing for one hour with 4 grams of NaOH (0.1 mol) in 80 gms of $H_2O$. Methanol and other volatiles were taken off until the temperature, with auxiliary heating, reached 100° C. The residue was diluted to 100 gms with water to give a 1 molal solution of $(Na)O_{1.5}Si(CH_2)_2S(CH_2)_2COONa$.

Example 2

Dimethylitaconate 24 gms (0.15 mol) and 18.2 gms of $(CH_3O)_3Si(CH_2)_2SH$ (0.1 mol) and 0.23 gms Na° in 10 ml of methanol were warmed to 100° C. for 1 hour after initially exothermic. The mixture was distilled under vacuum to give 21 gms (65 percent yield) of

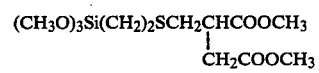

with a boiling point at 0.3 mm Hg pressure of 145°–155° C., $d_4^{21} = 1.55$ and $N_D^{25} = 1.4572$.

The product, 17 gms (0.05 mol) was saponified by refluxing with 4 gms of NaOH in 50 ml of $H_2O$ until a temperature of 100° C. was reached. The material was diluted to 50 gms with $H_2O$ to obtain 1 molal solution of

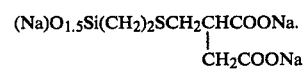

A titration indicated 0.02 equivalents of excess alkali.

EXAMPLE 3

An excess of $CH_2=CHSi(OCH_3)_3$ (200 gms, 1.35 mols) was stirred at 100°–110° C. while dropping in 100 gms (technical grade, 96–98 percent purity) of thioglycolic acid containing 1 gm of Vazo ® (azobisisobutyrolnitrile DuPont) free radical initiator. The reaction was exothermic. After one hour at 100°–110° C. the product was stripped to remove methanol (about 15 ml) and excess $CH_2=CHSi(OCH_3)_3$ to 100° C. The residue was a clear oil (230 gms) comprising partially hydrolyzed $(CH_3O)_3Si(CH_2)_2SCH_2COOH$ and $CH_2=CHSi(OCH_3)_3$. The product had an acid equivalent weight of 285 which incidates about 85 percent desired product and 15 percent vinylsiloxanes. The product retained a faint mercaptan odor. A solution of 28.5 gms of product in water was neutralized with NaOH and diluted to 100 gms to provide a 1 molal solution of $(Na)O_{1.5}SiCH_2CH_2SCH_2COONa$.

EXAMPLE 4

A solution of 15 gms of thiomalic acid (technical grade) (0.1 mol) in 30 gms of 1-methoxy-2-propanol and 15 gms of $CH_2CH=Si(OCH_3)_3$ with 0.5 gms of Luazo 82 (2-t-butylazo-2-cyanobutane) (Lucidol Div. of Pennwalt Corp., Buffalo, NY 14240) free radical initiator was warmed to 105° C. for one hour. There was a mild exotherm. The product was diluted with water to 100 gms to give a 1 molal solution of the free acid which was neutralized with 2 mol equivalents of NaOH to give the Na salt

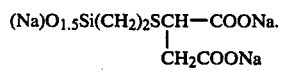

Aminoalkylsilanes were carboxylated by reaction with sodium chloroacetate in the presence of NaOH as the HCl acceptor or, by the addition of amino hydrogens to acrylate double bonds. Addition to acrylates is very rapid without additional catalyst, but addition to methacrylates and itaconates was much slower. Cyclic anhydrides react rapidly and completely with primary or secondary amines to form the corresponding acid amides. The following preparations are illustrative of such preparations.

EXAMPLE 5

To a solution of 22 gms of $(CH_3O)_3Si(CH_2)_3NH(CH_2)_2NH_2$ (0.1 mol) in 100 ml. of water was added 28.5 gms of $ClCH_2COOH$ (0.3 mols). To the stirred mixture was added 48 gms of 50 percent aqueous NaOH (0.6 mols) with cooling to keep the temperature below 50° C. The course of the reaction was followed by titrating 5 ml of product (0.5 molal) against 0.5 molal $CaCl_2$ with ammonium oxalate indicator to a cloudy end point.

| Time of Reaction | ml $CaCl_2$ | equivalent $Ca^{++}$ Product |
|---|---|---|
| After mixing | 1 | 0.2 |
| 6 hours at 50° C. | 5 | 1.0 |

Chelation of 1 mole of $Ca++$ per mole of product indicated complete reaction to the compound.

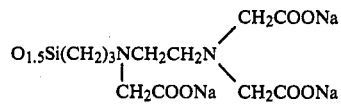

EXAMPLE 6

To a solution of 144 gms of acrylic acid in 364 gms of water was added 200 gms of technical grade $(CH_3O)_3Si(CH_2)_3NH(CH_2)_2NH_2$ and the mixture was refluxed for six hours. The course of the reaction was followed by thin layer chromatography on adsorbasil-1 silica. A spot of 1 percent aqueous product was eluted with methanol and sprayed with bromcresol-purple indicator. The initial mix showed an immobile alkaline spot (purple in color) of unreacted amine and an eluted band of the acid (yellow color). After 6 hours reflux there was only an immobile acid spot indicating that the acid was not part of the silane. The product was a 1.37 molal solution of

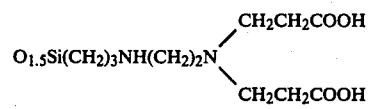

containing some

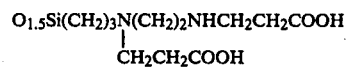

having a density of 1.125 g/mol at 20° C., and a viscosity of 50 cs. (0.5 Pa.s) at 25° C. A 73 gm portion was diluted to 100 gms with water to give a 1 molal solution of the acid adduct. 1 molal solutions of the acid were mixed with excess sodium silicate solutions in order to form the alkali metal salt in-situ. After aging one hour, the solutions were neutralized to pH 8.

EXAMPLE 7

In U.S. Pat. No. 3,337,496, there is disclosed mixtures of various siliconates with silicates as corrosion inhibitors in antifreeze solutions. It was observed that certain mixtures had improved stability to gelation. Ratios of siliconate to potassium silicate were relatively high ranging from 1:1 to 1:5 (50 to 20 mol percent siliconate). The pH was maintained at 10–11 and reserve alkalinity was maintained.

It has now been observed that the siliconate-silicates of this invention are stable even when the aqueous solution is treated with a neutralizing amount of mineral acid. Minimum stability of such materials is observed at a pH of about 8.

Sodium silicate "G" (a polysilicate having an $SiO_2/Na_2O$ weight ratio of 3.22, manufactured by Philadelphia Quartz, Philadelphia, PA) was used in the following manner:

A simple test was developed to compare the stabilizing capability of molal solutions of siliconate salts. One molal solutions of siliconate salt were mixed with 1 molal solutions of sodium silicate "G" and allowed to age for 16 hours at room temperature. They were then neutralized to pH 8 with 10 percent aqueous HCl and the time for gelation was observed. Compositions that did not gel in seven days were generally stable indefinitely. These materials are designated with an asterik in Table I below. Some compositions gave a delayed initial gelation, but the gel re-liquified to give stable solutions. They are shown in parentheses in the table below. A number of siliconate salts of the prior art were also evaluated. Samples B-I of Table I fall within the scope of this invention. Samples A and J-R fall outside the scope of this invention.

EXAMPLE 8

In a manner similar to Example 7, the salts of the nitrogen containing siliconates were evaluated using sodium silicate "G" (see Table II). Samples B-I fall within the scope of this invention while Samples A and J-O show similar materials but they fall outside the scope of this invention.

TABLE I

Stabilizing Capability of Siliconate Salts

| Ref. | Siliconate | Time to gellation at a mole ratio of siliconate to silicate | | | | |
|---|---|---|---|---|---|---|
| | | 1:5 | 1:7.5 | 1:10 | 1:15 | 1:20 |
| A | silicate alone** | — | — | — | — | — |
| B | $NaOOCCH_2SCH_2CH_2SiO_{1.5}(Na)$ | * | * | * | 2½ min. | 90 sec |
| C | $NaOOCCH_2SCH_2CH_2SiO_{1.5}(Na)$ | 2 days | 30 sec. | 30 sec. | — | — |
| D | $NaOOCCH_2CH_2SCH_2CH_2SiO_{1.5}(Na)$ | " | 12 hrs. | 30 sec. | 20 sec. | 15 sec. |
| E | $NaOOCCH_2CH_2SCH_2CH_2CH_2SiO_{1.5}(Na)$ | 2 days | 25 min. | 30 sec. | — | — |
| F | $NaOOCCHSCH_2CH_2SiO_{1.5}(Na)$ <br> \|<br> $CH_2COONa$ | * | * | * | 10 min. | 90 sec. |
| G | $NaOOCCHSCH_2CH_2CH_2SiO_{1.5}(Na)$ <br> \|<br> $CH_2COONa$ | * | (½ hr.⟶*) | 90 sec. | — | — |
| H | $NaOOCCHCH_2SCH_2CH_2SiO_{1.5}(Na)$ <br> \|<br> $CH_2COONa$ | * | * | * | 1½ hr. | 1 min. |
| I | $NaOOCCHCH_2SCH_2CH_2CH_2SiO_{1.5}(Na)$ <br> \|<br> $CH_2COONa$ | * | * | * | 1½ hr. | 40 sec. |
| J | $CH_3SiO_{1.5}(Na)$ | 35 sec. | — | — | — | — |
| K | $C_6H_5SiO_{1.5}(Na)$ | 15 sec. | — | — | — | — |
| L | $HSCH_2CH_2SiO_{1.5}(Na)$ | 40 sec. | — | — | — | — |
| M | $CNCH_2CH_2SiO_{1.5}(Na)$ | 20 sec. | — | — | — | — |
| N | $O{-}CH_2CHCH_2O(CH_2)_3SiO_{1.5}(Na)$ (epoxy) | 2 min. | — | — | — | — |
| O | $HOCH_2CHCH_2OCH_2CHOHCH_2O(CH_2)_3SiO_{1.5}(Na)$<br>\|<br>$OH$ | 3 min. | — | — | — | — |
| P | $NaOOCCH_2CH_2CH_2SiO_{1.5}(Na)$ | * | 30 min. | 4 min. | — | — |
| Q | $NaOP{=}O(CH_3)OCH_2CH_2CH_2SiO_{1.5}(Na)$ | * | 9 min. | 2 min. | — | — |
| R | $NaO_2C(CH_2)_2S(CH_2)_3SiO_{1.5}(Na)$ | 45 sec. | — | — | — | — |

**control - no siliconate present - gelled in 2 sec.
*indicates at least 7 days stability
parentheses indicates initial gellation, but re-liquification to give a stable solution.

TABLE II

Stabilizing Capability of Salts of Nitrogen Containing Siliconates

| Ref. | Siliconate | Time to gellation at mole ratio of siliconate to silicate | | | | |
|---|---|---|---|---|---|---|
| | | 1:5 | 1:75 | 1:10 | 1:15 | 1:20 |
| A | silicate alone | — | — | — | — | — |
| B | $(NaOOCCH_2)_2N(CH_2)_3SiO_{1.5}(Na)$ | * | (25 min⟶*) | 45 sec. | — | — |
| C | $NaOOCCHCH_2NH(CH_2)_3SiO_{1.5}(Na)$<br>\|<br>$CH_2COONa$ | * | 8 hr. | 2 min. | 15 sec. | — |
| D | $(NaOOCCH_2CH_2)_2N(CH_2)_3SiO_{1.5}(Na)$ | * | * | 2 min | — | — |
| E | $(NaOOCCH_2)_2N(CH_2)_2NH(CH_2)_3SiO_{1.5}(Na)$ | * | 6 min. | 90 sec. | — | — |
| F | $(NaOOCCH_2)_2N(CH_2)_2N(CH_2)_3SiO_{1.5}(Na)$<br>\|<br>$CH_2COONa$ | * | * | * | (4 min⟶*) | — |
| G | $(NaOOCH_2CH_2)_2NCH_2CH_2NH(CH_2)_3SiO_{1.5}(Na)$ | * | * | * | 1 min. | 10 sec. |

TABLE II-continued

Stabilizing Capability of Salts of Nitrogen Containing Siliconates

| Ref. | Siliconate | Time to gellation at mole ratio of siliconate to silicate | | | | |
|---|---|---|---|---|---|---|
| | | 1:5 | 1:75 | 1:10 | 1:15 | 1:20 |
| H | NaOOCCHCH$_2$NH(CH$_2$)$_2$NH(CH$_2$)$_3$SiO$_1.5$(Na)<br>$\|$<br>CH$_2$COONa | * | 8 hrs. | 2 min. | 15 sec. | — |
| I | (NaOOCCH$_2$CH$_2$)$_2$NCH$_2$CH$_2$N(CH$_2$)$_3$SiO$_1.5$(Na)<br>$\|$<br>CH$_2$CH$_2$COONa | * | * | * | (15 min→*) | 90 sec. |
| J | NaOOCCH$_2$NH(CH$_2$)$_3$SiO$_1.5$(Na) | 9 min. | — | — | — | — |
| K | NaOOC(CH$_2$)$_2$NH(CH$_2$)$_3$SiO$_1.5$(Na) | † | — | — | — | — |
| L | NaOOCCH=CHC=ON(CH$_2$)$_3$SiO$_1.5$(Na)<br>$\|$<br>H | † | — | — | — | — |
| M | NaOOCCH$_2$NH(CH$_2$)$_2$NH(CH$_2$)$_3$SiO$_1.5$(Na) | 10 sec. | — | — | — | — |
| N | NaOOCH$_2$CH$_2$NHCH$_2$CH$_2$NH(CH$_2$)$_3$SiO$_1.5$(Na) | † | — | — | — | — |
| O | NaOOCCH$_2$NHCH$_2$CH$_2$NCH$_2$CHOHCH$_2$O(CH$_2$)$_3$SiO$_1.5$(Na)<br>$\|$<br>CH$_2$COONa | * | 3 min. | 1 min. | — | — |

*indicates at least 7 days stability
**control - no siliconate present - gelled in 2 seconds
parentheses indicates initial gellation, but re-liquification to give a stable solution.
" " indicates initial incompatibility

EXAMPLE 9

The siliconate salts were evaluated as additives to antifreeze systems by utilizing the ASTM test method D-1384. Prestone ® II, Union Carbide commercial antifreeze was used as a comparative example. ASTM D-1384 test method requires that each test be run in triplicate. For the purposes herein, the test was run only once as a rough screening test. The corrosive water used in the test consisted of 100 ppm each of sodium sulfate, sodium chloride and sodium bicarbonate. Metals tested included copper, solder, brass, steel, cast iron and cast aluminum. A control was run using each of these metals without any additive. Test solutions were prepared using 250 gms of ethylene glycol and 500 gms of the corrosion water prepared as above.

The metal strips were as assembled as set forth in the ASTM test procedure and these assembled metals were immersed in the test solution. The beakers containing the test solutions and metal assemblies were heated to 88° C. and aerated at 100 ml/min. for a period of two weeks. The pH of the test solution was determined both before and after the test. Weight measurements were taken on each metal to the nearest milligram after the test strips were cleaned with water and pumice soap and an acetone rinse. After the testing, weight loss calculations were made on the samples after they were cleaned with water and pumice soap using a soft brass bristle brush and acetone rinse. In some cases, the weight was recorded as a gain because of inadequate cleaning techniques.

| reference | type of Siliconate | Siliconate weight percent amount used | weight loss by corrosion in mg | | | | | |
|---|---|---|---|---|---|---|---|---|
| | | | copper | solder | brass | steel | cast iron | cast aluminum |
| Control A (Prestone ® II) | — | 0 — | 27.5 0.5 | 117.2 2.8 | 57.7 0.9 | 434.3 0.9 | 535.9 1.4 | 28.7 0.3 |
| Control B | (Na)$_{1.5}$OSiCH$_2$CH$_2$—SCH$_2$COONa | 0 0.5 | 0.7 14.1 | 102.1 12.2 | +0.1 0.4 | 792.6 0.7 | 694.7 0.5 | 27.5 +4.6 |
| Control C* | (Na)$_{1.5}$OSi(CH$_2$)$_3$—NHCH$_2$CH$_2$N(CH$_2$CH$_2$COONa)$_2$ | 0 0.5 | 0.8 32.3 | 99.1 24.6 | 0.2 0.2 | 317.2 +1.6 | 406.5 +3.2 | 12.8 +52.9 |

*some precipitate noted at the end of the test

That which is claimed is:
1. A method of stabilizing soluble silicates comprising adding to the soluble silicates a siliconate selected from a group consisting essentially of
   (I) a siliconate having the general formula

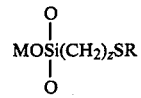

and
   (II) a siliconate having the general formula

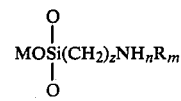

wherein in both formulas, M is selected from a group consisting essentially of
(i) alkali metal cations and
(ii) tetraorganoammonium cations and z has a value of 2 or 3,
wherein in formula (I), R is selected from a group consisting essentially of —CH$_2$COOM, —CH$_2$CH$_2$COOM,

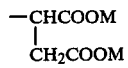 and 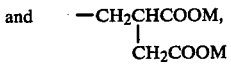

and wherein in formula (II), n has a value of 0 or 1; m has a value of 1 or 2, the sum of n+m is 2 and R is selected from a group consisting essentially of —CH$_2$COOM, —CH$_2$CH$_2$COOM,

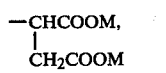 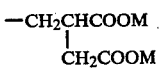

and —(CH$_2$)$_2$N(CH$_2$COOM)$_2$
when n is 0 and m is 2, and R is selected from a group consisting essentially of

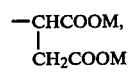 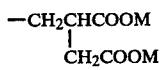

and (CH$_2$)$_z$NH$_p$R'$_q$ when n is 1 and m is 1, p has a value of 0 or 1, q has a value of 1 or 2 and the sum of p+q is 2 wherein R' is selected from a group consisting of

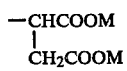 and 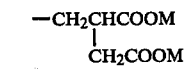

when p is 1 and q is 1 and R' is selected from a group consisting of —CH$_2$COOM, —CH$_2$CH$_2$COOM,

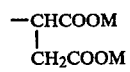 and 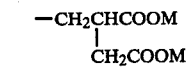

when p is 0 and q is 2, wherein M and z have the same meaning as set forth above.

2. A method as claimed in claim 1 wherein the siliconate has the formula

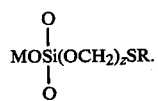

3. A method as claimed in claim 2 wherein M is an alkali metal and z is 2.
4. A method as claimed in claim 3 wherein M is an alkali metal and z is 3.
5. A method as claimed in claim 3 wherein the alkali metal is sodium.
6. A method as claimed in claim 3 wherein the alkali metal is potassium.
7. A method as claimed in claim 4 wherein the alkali metal is sodium.
8. A method as claimed in claim 4 wherein the alkali metal is potassium.

9. A method as claimed in claim 2 wherein M is a tetraorganoammonium radical.
10. A method as claimed in claim 9 wherein the tetraorganoammonium radical is a tetraalkylammonium radical.
11. The method as claimed in claim 10 wherein the tetraalkylammonium radical is tetramethylammonium.
12. A method as claimed in claim 1 wherein the siliconate has the formula

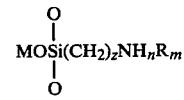

13. A method as claimed in claim 12 wherein M is an alkali metal and z is 2.
14. A method as claimed in claim 12 wherein M is an alkali metal and z is 3.
15. A method as claimed in claim 13 wherein the alkali metal is sodium.
16. A method as claimed in claim 13 wherein the alkali metal is potassium.
17. A method as claimed in claim 14 wherein the alkali metal is sodium.
18. A method as claimed in claim 14 wherein the alkali metal is potassium.
19. A method as claimed in claim 12 wherein M is a tetraorganoammonium radical.
20. A method as claimed in claim 19 wherein the tetraorganoammonium radical is a tetraalkylammonium radical.
21. A method as claimed in claim 20 wherein the tetraalkylammonium radical is tetramethylammonium.
22. A method as claimed in claim 1 wherein M in each case is sodium.
23. A method as claimed in claim 1 wherein M in each case is potassium.
24. A method as claimed in claim 1 wherein M in each case is a tetraalkylammonium cation.
25. A method as claimed in claim 24 wherein the tetraalkylammonium cation is a tetra(methyl)ammonium cation.
26. An alcohol composition comprising a combination of
(A) an alcohol;
(B) a corrosion inhibiting amount of a composition which is selected from a group consisting of
(I) a siliconate having the general formula

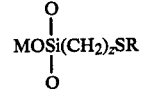

and
(II) a siliconate having the general formula

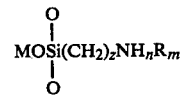

wherein in both formulas, M is selected from a group consisting essentially of
(i) alkali metal cations and (ii) tetraorganoammonium cations and z has a value of 2 or 3, wherein in formula (I), R is selected from a group consisting essentially of —CH$_2$COOM, —CH$_2$CH$_2$COOM,

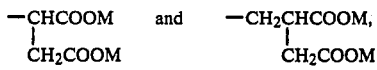

and wherein in formula (II), n has a value of 0 or 1; m has a value of 1 or 2, the sum of n+m is 2 and R is selected from a group consisting essentially of —CH$_2$COOM, —CH$_2$CH$_2$COOM,

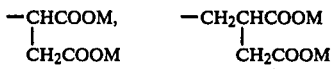

and —(CH$_2$)$_2$N(CH$_2$COOM)$_2$ when n is 0 and m is 2, and R is selected from a group consisting essentially of

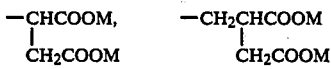

and (CH$_2$)$_z$NH$_p$R'$_q$ when n is 1 and m is 1, p has a value of 0 or 1, q has a value of 1 or 2 and the sum of p+q is 2, and (C) a soluble silicate represented by the general formula

wherein M has the meaning above and a has a value of 1-3 and (D) water.

27. An aqueous alcohol composition as claimed in claim 26 comprising (A) 85 to 98 percent by weight of alkylene glycol,
(B) 0.01 to 0.5 percent by weight of a siliconate,
(C) 0.025 to 1.0 percent by weight of an alkali metal silicate, and
(D) the remainder being water.

28. An aqueous alcohol composition as claimed in claim 27 wherein the siliconate has the formula

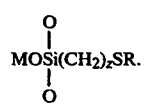

29. An aqueous alcohol composition as claimed in claim 28 wherein M is an alkali metal.

30. An aqueous alcohol composition as claimed in claim 29 wherein the alkali metal is sodium.

31. An aqueous alcohol composition as claimed in claim 29 wherein the alkali metal is potassium.

32. A composition as claimed in claim 30 wherein the siliconate is NaOOCH$_2$SCH$_2$CH$_2$SiO$_{1.5}$(Na).

33. A composition as claimed in claim 30 wherein the siliconate is

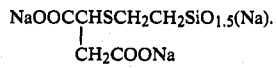

34. A composition as claimed in claim 30 wherein the siliconate is

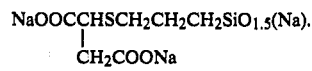

35. A composition as claimed in claim 30 wherein the siliconate is

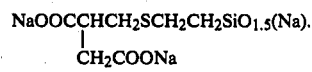

36. A composition as claimed in claim 30 wherein the siliconate is

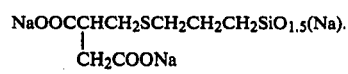

37. A composition as claimed in 31 wherein the siliconate is KOOCCH$_2$SCH$_2$CHhd 2SiO$_{1.5}$(K).

38. A composition as claimed in claim 31 wherein the siliconate is

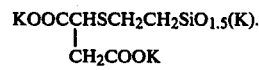

39. A composition as claimed in claim 31 wherein the siliconate is

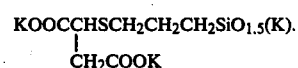

40. A composition as claimed in claim 31 wherein the siliconate is

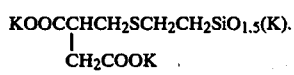

41. A composition as claimed in claim 31 wherein the siliconate is

42. An aqueous alcohol composition as claimed in claim 28 wherein M is a tetraorganoammonium radical.

43. An aqueous alcohol composition as claimed in claim 42 wherein the tetraorganoammonium radical is a tetraalkylammonium radical.

44. An aqueous alcohol composition as claimed in claim 43 wherein the tetraalkylammonium radical is tetramethylammonium and M is sodium.

45. An aqueous alcohol composition as claimed in claim 43 wherein the tetraalkylammonium radical is tetramethylammonium and M is potassium.

46. An aqueous alcohol composition as claimed in claim 28 wherein component (A) is ethylene glycol.

47. An aqueous alcohol composition as claimed in claim 29 wherein component (A) is ethylene glycol.
48. An aqueous alcohol composition as claimed in claim 30 wherein component (A) is ethylene glycol.
49. An aqueous alcohol composition as claimed in claim 31 wherein component (A) is ethylene glycol.
50. An aqueous alcohol composition as claimed in claim 28 wherein component (A) is propylene glycol.
51. An aqueous alcohol composition as claimed in claim 29 wherein component (A) is propylene glycol.
52. An aqueous alcohol composition as claimed in claim 30 wherein component (A) is propylene glycol.
53. An aqueous alcohol composition as claimed in claim 31 wherein component (A) is propylene glycol.
54. An aqueous alcohol composition as claimed in claim 27 wherein the siliconate has the formula

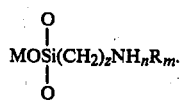

$$MOSi(CH_2)_zNH_nR_m.$$

55. An aqueous alcohol composition as claimed in claim 54 wherein M is an alkali metal.
56. An aqueous alcohol composition as claimed in claim 55 wherein the alkali metal is sodium.
57. An aqueous alcohol composition as claimed in claim 55 wherein the alkali metal is potassium.
58. A composition as claimed in claim 56 wherein the siliconate is $(NaOOCCH_2)_2N(CH_2)_3SiO_{1.5}(Na)$.
59. A composition as claimed in claim 56 wherein the siliconate is

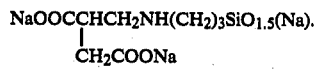

$NaOOCCHCH_2NH(CH_2)_3SiO_{1.5}(Na)$.
   |
   $CH_2COONa$

60. A composition as claimed in claim 56 wherein the siliconate is $(NaOOCCH_2CH_2)_2N(CH_2)_3SiO_{1.5}(Na)$.
61. A composition as claimed in claim 56 wherein the siliconate is $(NaOOCCH_2)_2N(CH_2)_2NH(CH_2)_3SiO_{1.5}-(Na)$.
62. A composition as claimed in claim 56 wherein the siliconate is

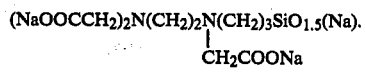

$(NaOOCCH_2)_2N(CH_2)_2N(CH_2)_3SiO_{1.5}(Na)$.
   |
   $CH_2COONa$

63. A composition as claimed in claim 56 wherein the siliconate is $(NaOOCH_2CH_2)_2NCH_2CH_2NH(CH_2)_3SiO_{1.5}(Na)$.
64. A composition as claimed in claim 56 wherein the siliconate is

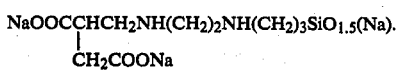

$NaOOCCHCH_2NH(CH_2)_2NH(CH_2)_3SiO_{1.5}(Na)$.
   |
   $CH_2COONa$

65. A composition as claimed in claim 56 wherein the siliconate is

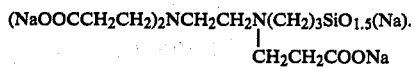

$(NaOOCCH_2CH_2)_2NCH_2CH_2N(CH_2)_3SiO_{1.5}(Na)$.
   |
   $CH_2CH_2COONa$

66. A composition as claimed in claim 57 wherein the siliconate is $(KOOCCH_2)_2N(CH_2)_3SiO_{1.5}(K)$.

67. A composition as claimed in claim 57 wherein the siliconate is $KOOCCHCH_2NH(CH_2)_3SiO_{1.5}(K)$.
68. A composition as claimed in claim 57 wherein the siliconate is $(KOOCCH_2CH_2)_2N(CH_2)_3SiO_{1.5}K$.
69. A composition as claimed in claim 57 wherein the siliconate is $(KOOCCH_2)_2N(CH_2)_2NH(CH_2)_3SiO_{1.5}K$.
70. A composition as claimed in claim 57 wherein the siliconate is

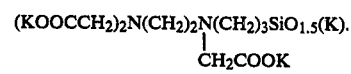

$(KOOCCH_2)_2N(CH_2)_2N(CH_2)_3SiO_{1.5}(K)$.
   |
   $CH_2COOK$

71. A composition as claimed in claim 57 wherein the siliconate is $(KOOCH_2CH_2)_2NCH_2CH_2NH(CH_2)_3SiO_{1.5}(K)$.
72. A composition as claimed in claim 57 wherein the siliconate is

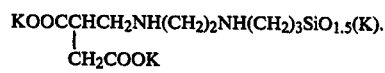

$KOOCCHCH_2NH(CH_2)_2NH(CH_2)_3SiO_{1.5}(K)$.
   |
   $CH_2COOK$

73. A composition as claimed in claim 57 wherein the siliconate is

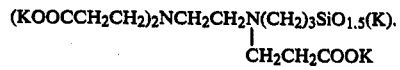

$(KOOCCH_2CH_2)_2NCH_2CH_2N(CH_2)_3SiO_{1.5}(K)$.
   |
   $CH_2CH_2COOK$

74. An aqueous alcohol composition as claimed in claim 54 wherein M is a tetraorganoammonium radical.
75. An aqueous alcohol composition as claimed in claim 74 wherein the tetraorganoammonium radical is a tetraalkylammonium radical.
76. An aqueous alcohol composition as claimed in claim 75 wherein the tetraalkylammonium radical is tetramethylammonium and M is sodium.
77. An aqueous alcohol composition as claimed in claim 75 wherein the tetraalkylammonium radical is tetramethylammonium and M is potassium.
78. A composition as claimed in claim 54 wherein component (A) is ethylene glycol.
79. An aqueous alcohol composition as claimed in claim 55 wherein component (A) is ethylene glycol.
80. An aqueous alcohol composition as claimed in claim 56 wherein component (A) is ethylene glycol.
81. An aqueous alcohol composition as claimed in claim 57 wherein component (A) is ethylene glycol.
82. An aqueous alcohol composition as claimed in claim 54 wherein component (A) is propylene glycol.
83. An aqueous alcohol composition as claimed in claim 55 wherein component (A) is propylene glycol.
84. An aqueous alcohol composition as claimed in claim 56 wherein component (A) is propylene glycol.
85. An aqueous alcohol composition as claimed in claim 57 wherein component (A) is propylene glycol.
86. A method of inhibiting metal corrosion in an aqueous medium by adding to the aqueous medium a composition consisting of a siliconate selected from a group consisting of
(I) a siliconate having the general formula

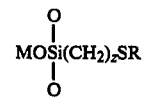

$$MOSi(CH_2)_zSR$$

and
(II) a siliconate having the general formula

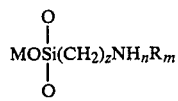

wherein in both formulas, M is selected from a group consisting essentially of
(i) alkali metal cations and
(ii) tetraorganoammonium cations and z has a value of 2 or 3,
wherein in formula (I), R is selected from a group consisting essentially of —CH$_2$COOM, —CH$_2$CH$_2$COOM,

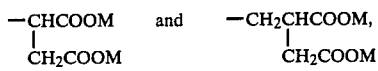

and wherein in formula (II), n has a value of 0 or 1; m has a value of 1 or 2, the sum of n+m is 2 and R is selected from a group consisting essentially of —CH$_2$COOM, —CH$_2$CH$_2$COOM,

and —(CH$_2$)$_2$N(CH$_2$COOM)$_2$ when n is 0 and m is 2, and R is selected from a group consisting essentially of

and (CH$_2$)$_z$NH$_p$R′$_q$ when n is 1 and m is 1, p has a value of 0 or 1, q has a value of 1 or 2 and the sum of p+q is 2 wherein R′ is selected from a group consisting of

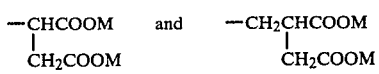

when p is 1 and q is 1 and R′ is selected from a group consisting of —CH$_2$COOM, —CH$_2$CH$_2$COOM,

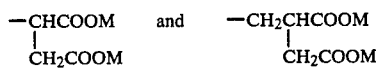

when p is 0 and q is 2, wherein M and Z have the same meaning as set forth above.

87. A method as claimed in claim 86 wherein there is also present a soluble silicate represented by the general formula

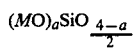

wherein M has the meaning above and a has a value of 1-3.

88. A method as claimed in claim 86 wherein the siliconate has the formula

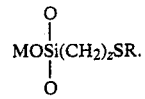

89. A method as claimed in claim 88 wherein M in the siliconate is an alkali metal.

90. A method as claimed in claim 89 wherein the alkali metal is sodium.

91. A method as claimed in claim 90 wherein the siliconate is

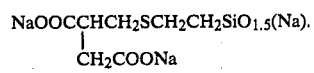

92. A method as claimed in claim 89 wherein the alkali metal is potassium.

93. A composition as claimed in claim 92 wherein the siliconate is

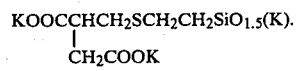

94. A method as claimed in claim 86 wherein the siliconate has the formula

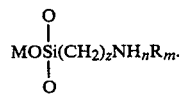

95. A method as claimed in claim 94 wherein M in the siliconate is an alkali metal.

96. A method as claimed in claim 95 wherein the alkali metal is sodium.

97. A method as claimed in claim 95 wherein the alkali metal is potassium.

98. A composition as claimed in claim 96 wherein the siliconate is

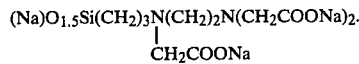

99. A composition as claimed in claim 97 wherein the siliconate is

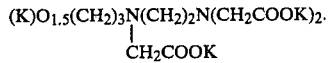

100. A composition of matter comprising
(A) 0.1 to 20 mole percent of a siliconate selected from a group consisting essentially of
(I) a siliconate having the general formula

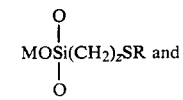

(II) a siliconate having the general formula

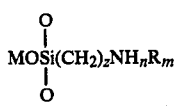

wherein in both formulas, M is selected from a group consisting essentially of
  (i) alkali metal cations and
  (ii) tetraorganoammonium cations and z has a value of 2 or 3,
wherein in formula (I), R is selected from a group consisting essentially of —CH₂COOM, —CH₂CH₂COOM,

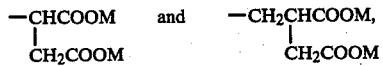

and wherein in formula (II), n has a value of 0 or 1; m has a value of 1 or 2, the sum of n+m is 2 and R is selected from a group consisting essentially of —CH₂COOM, —CH₂CH₂COOM,

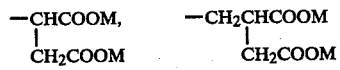

and —(CH₂)₂N(CH₂COOM)₂ when n is 0 and m is 2, and R is selected from a group consisting essentially of

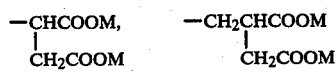

and (CH₂)$_z$NH$_p$R'$_q$ when n is 1 and m is 1, p has a value of 0 or 1, q has a value of 1 or 2 and the sum of p+q is 2, and (B) 80 to 99.9 mole percent of a soluble silicate represented by the general formula

wherein M has the meaning above and a has a value of 1–3.

101. A composition of matter as claimed in claim 100 wherein the siliconate has the formula

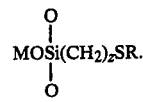

102. A composition of matter as claimed in claim 101 wherein M is an alkali metal.

103. A composition of matter as claimed in claim 102 wherein the alkali metal is sodium.

104. A composition of matter as claimed in claim 102 wherein the alkali metal is potassium.

105. A composition as claimed in claim 103 wherein the siliconate is

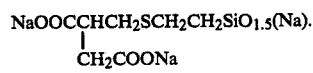

106. A composition as claimed in claim 104 wherein the siliconate is

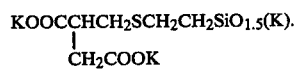

107. A composition as claimed in claim 100 wherein the siliconate has the formula

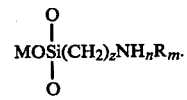

108. A composition as claimed in claim 107 wherein M in the siliconate is an alkali metal.

109. A composition as claimed in claim 108 wherein the alkali metal is sodium.

110. A composition as claimed in claim 108 wherein the alkali metal is potassium.

111. A composition as claimed in claim 109 wherein the siliconate is

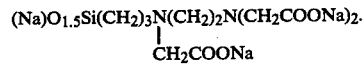

112. A composition as claimed in claim 110 wherein the siliconate is

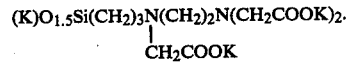

* * * * *

UNITED STATES PATENT AND TRADEMARK OFFICE
CERTIFICATE OF CORRECTION

PATENT NO. : 4,344,860

DATED : August 17, 1982

INVENTOR(S) : Edwin P. Plueddemann

It is certified that error appears in the above-identified patent and that said Letters Patent is hereby corrected as shown below:

In column 4, line 34, "$(CH_{21})_z NH_p R'_q$" should read -- $(CH_2)_z NH_p R'_q$ --.

In column 5, line 24, "g has a value of" should read
 -- q has a value of --.

In column 12, line 10, "200 gms" should read -- 220 gms --.

In column 12, line 20, "was not part" should read -- was now part --.

In column 14, "Table I", "(½ hr. $\longrightarrow$ *)" should read --(1½ hr. $\longrightarrow$ *) --.

In column 15, "Table II" at the bottom,
 " " " indicates initial incompatability" should read
 -- "$+$" indicates initial incompatability --.

In column 20, line 27, "CHhd 2Si" should read -- $CH_2Si$ --.

Signed and Sealed this

Twelfth Day of February 1985

[SEAL]

Attest:

DONALD J. QUIGG

*Attesting Officer*     *Acting Commissioner of Patents and Trademarks*